United States Patent [19]

Bolger et al.

[11] Patent Number: 5,437,290
[45] Date of Patent: Aug. 1, 1995

[54] SYSTEM AND METHOD FOR MONITORING INTRALUMINAL DEVICE POSITION

[75] Inventors: Ann F. Bolger, Menlo Park; Chris Tacklind, Palo Alto, both of Calif.

[73] Assignee: Board of Trustees of the Leland Stanford Jr. University, Palo Alto, Calif.

[21] Appl. No.: 62,670

[22] Filed: May 14, 1993

Related U.S. Application Data

[63] Continuation-in-part of Ser. No. 755,992, Sep. 6, 1991, abandoned.

[51] Int. Cl.6 .............................................. A61B 5/00
[52] U.S. Cl. .................................... 128/898; 604/53; 604/280; 128/656
[58] Field of Search ...................... 364/413.13, 413.22; 128/656–658, 898; 604/53, 280

[56] References Cited

U.S. PATENT DOCUMENTS

| | | |
|---|---|---|
| 3,399,668 | 9/1968 | Lundgren . |
| 3,605,750 | 9/1971 | Sheridan et al. . |
| 3,847,157 | 11/1974 | Caillouette et al. . |
| 4,096,862 | 6/1978 | DeLuca . |
| 4,273,110 | 6/1981 | Groux . |
| 4,279,252 | 7/1981 | Martin . |
| 4,416,289 | 11/1983 | Bresler . |
| 4,431,005 | 2/1984 | McCormick . |
| 4,796,637 | 1/1989 | Mascuch et al. . |
| 4,838,879 | 6/1989 | Tanabe et al. . |
| 4,863,423 | 9/1989 | Wallace . |
| 4,922,924 | 5/1990 | Gambale et al. . |
| 5,004,456 | 4/1991 | Botterbusch et al. . |
| 5,034,005 | 7/1991 | Appling . |
| 5,036,464 | 7/1991 | Gillies et al. ............ 364/413.22 |
| 5,099,846 | 3/1992 | Hardy ..................... 364/413.22 |
| 5,144,959 | 9/1992 | Gambale et al. . |
| 5,147,317 | 9/1992 | Shank et al. . |

*Primary Examiner*—Randall L. Green
*Assistant Examiner*—Rob Clarke
*Attorney, Agent, or Firm*—Townsend and Townsend Khourie and Crew

[57] ABSTRACT

The penetration depth of an intraluminal device, such as a transesophageal probe or a vascular catheter, is monitored by totalizing incremental advancement and withdrawal of the device over time. For a first embodiment, the devices are provided with axially spaced-apart markings along at least a portion of their lengths. The penetration depth of such intraluminal devices into a body lumen is monitored by detecting passage of the markings past a fixed location relative to the body lumen. Usually, the markings will be optically detected in a manner which permits forward and retrograde motion to be distinguished. Thus, the net totalization of the markers will correspond to the actual penetration distance in real time. In an alternate embodiment, the incremental advancement and withdrawal may be followed by use of a contact roller. In either case, the distance can be displayed by itself or in combination with a real time image, with the distance and image optionally being recorded.

12 Claims, 9 Drawing Sheets

| POSITION | X | Y |
|----------|---|---|
| A | 0 | 1 |
| B | 0 | 0 |
| C | 1 | 0 |
| D | 1 | 1 |

SYSTEM AND METHOD FOR MONITORING INTRALUMINAL DEVICE POSITION

This application is a continuation-in-part of application Ser. No. 07/755,992, filed on Sep. 6, 1991, now abandoned, the full of disclosure of which is incorporated herein by reference.

BACKGROUND OF THE INVENTION

1. Field of the Invention

The present invention relates generally to methods and apparatus for monitoring the penetration distance of an elongate device inserted into a body lumen during a medical procedure. More particularly, the present invention relates to real time detection and position monitoring of the device as it passes by a location fixed relative to the lumen.

Catheters, esophageal probes, endoscopes, and other medical devices are frequently introduced into body lumens for a variety of purposes, including imaging and interventional therapy. For many such procedures, it is necessary to accurately monitor the position of the catheter, particularly the distal end of the catheter which is remote from the entry point. For example, it is frequently necessary to know the precise location of the distal tip of a device in order to perform a subsequent interventional procedure, to facilitate interchange of devices, and to track the precise location of a device during the course of a single procedure.

The most common positional monitoring techniques rely on fluoroscopic imaging of radiopaque markers on the device. While such fluoroscopic techniques are well suited for observing the progress of a device as it is being inserted, particularly for monitoring the manipulation of intravascular catheters through various branches of the vascular system, such techniques are limited in several respects. In many situations, fluoroscopic imaging equipment is not available and it would be desirable to have other means for providing accurate, real time monitoring of device penetration. Moreover, a visual fluoroscopic image is difficult to record to provide a permanent record of device position. Such visual positional information is also inaccurate since the apparent location of the distal end of a device may change depending on the patient's position relative to the imaging equipment. Additionally, fluoroscopic images can be difficult to coordinate with images produced by other procedures, particularly ultrasonic imaging procedures which employ a separate CRT screen presenting a quite different view of the imaged area.

Heretofore, the penetration depth of elongate medical devices, such as catheters and probes, has usually been monitored visually by the physician observing scale markings which have been placed on the side of the device. That is, the physician will simply look at the device at the point of entry and read the approximate penetration depth from the scale. While this approach has the advantage of simplicity, it does suffer from numerous limitations which restrict its effectiveness in modern medical procedures.

First, the accuracy of penetration which can be determined is limited by the lack of a fixed location against which to read the scale. The accuracy is further limited by the relatively broad spacing between scale markings which are required to permit visual reading. The visual reading of the scale further requires that the physician turn away from other areas where attention should be directed and attempt to read the markings, often in diminished light as required by many procedures. Each reading which is obtained requires additional time to be recorded and becomes obsolete as soon as the device is moved in any fashion. As a result, coordination between the penetration depth at any given time and other images can be problematic. Finally, the visual reading of a penetration depth does not lend itself to permanent recording, particularly in combination with other imaging techniques, such as ultrasonic images which are frequently recorded on video tape.

For these reasons, it would be desirable to provide improved methods and systems for monitoring intraluminal penetration depth of medical devices used during various medical procedures. Such monitoring should provide very accurate determination of depth, preferably on a real time basis. The system should be highly repeatable so that the devices can be withdrawn, interchanged, and reintroduced with assurance that the distal end of the device will be returned precisely to a desired location. The penetration depth information should be provided in a form which is amenable to digital display, recording, and preferably to recording in combination with other imaging procedures, such as ultrasonic imaging procedures. Additionally, the depth monitoring should not require effort of the physician beyond reading a convenient display of penetration depth, optionally in combination with other imaging information.

2. Description of the Background Art

U.S. Pat. No. 5,004,456, describes an anesthetic administration catheter having spaced-apart markings along its length to provide a visual indication of penetration depth. U.S. Pat. No. 3,399,668, describes a cholangiography catheter having equally spaced-apart indicia to permit the physician to determine the extent of insertion. U.S. Pat. Nos. 4,838,879, and 4,279,252, describe catheters having spaced-apart opaque rings along their lengths to permit calculation of image magnification. U.S. Pat. No. 3,605,750, describes an endotracheal tube having three designations along its length corresponding to three particular penetration depths. U.S. Pat. Nos. 4,431,005; 4,416,289; 4,096,862; and 3,847,157, describe catheters having magnetic and radioactive markers which can be located using external monitoring equipment.

SUMMARY OF THE INVENTION

The present invention provides methods, apparatus, and systems for monitoring the penetration distance of a medical device, such as a catheter or probe, into a body lumen, such as a blood vessel, the esophagus, the colon, the ureter, or the like. The penetration measurement is highly accurate and can be provided as a continuous (real time) digital signal which can be converted directly into a digital display or combined with other imaging information and presented on a conventional monitor, such as a CRT. In addition to accuracy, the measured penetration distances provided by the present invention are highly repeatable so that devices may be withdrawn, exchanged, and returned very accurately to any position which was monitored earlier in the procedure. Moreover, the present invention does not require visual assessment of the penetration distance by the physician, leading to less error, and automatic recording of the information minimizes distraction of the physician during the procedure.

The method of the present invention relies on measuring the net distance traveled by the medical device past a fixed location relative to the body lumen. In particular, the distance traveled is measured incrementally as the device is advanced one or more times past the fixed location and also as the device is withdrawn one or more times past the fixed location. By continuously totalizing the incremental distances advanced and the incremental distances withdrawn, a value is produced which corresponds to the net penetration distance of the device in the body lumen over real time.

In a particular aspect, the method of the present invention relies on detection, usually by optical means, of the passage of axially spaced-apart markings on the device past a fixed location relative to the lumen as the device is incrementally advanced and withdrawn. A signal is produced in response to the passage of each marking, and the number of "signal passages" totalized to produce a value which corresponds to the net penetration distance of the device in real time. Preferably, the signals are totalized by determining the direction of movement of the device and incrementing or decrementing the total accumulated distance based on the number of signals and the direction of movement, i.e., movement in one direction will increase the accumulated distance while movement in the other direction will decrease the accumulated distance. Thus, by selecting the distance at which the markings are spaced-apart, a desired level of accuracy can be achieved.

In a second particular aspect, the method of the present invention relies on contacting a roller disposed at a fixed location relative to the body lumen against the device as said device is advanced and withdrawn past the fixed location. The number of roller rotations (including partial rotations) in each direction is sensed, and the net number of roller rotations totalized to produce a value which corresponds to the penetration distance in real time.

The penetration distance may be measured from different datum points, including but not limited to the fixed location at which the markings are detected or the roller is disposed. If datums other than the fixed location are desired, the total distance can be "zeroed" when the probe (or a particular marker thereon) has reached the desired datum. The use of datum points which are clearly apparent by imaging techniques such as fluoroscopic or ultrasonic imaging, enhances the accuracy of distance measurement, particularly when comparing penetration of devices which have been introduced through percutaneous penetrations made at different times.

In a particular aspect of the present invention, the direction of movement of the device is determined by comparing a preselected characteristic of successive markings which pass by the detection location. Usually, successive markings will have one of two easily observed characteristics, e.g., a narrow band width and wide band width. So long as markings which successively pass the location display an alternating pattern of such characteristics, i.e., broad followed by narrow followed by broad, etc., continued movement in a first direction is assumed. As soon as the same preselected characteristic is observed in two successive markings, i.e., broad followed by broad or narrow followed by narrow, then it is known that the direction of the catheter has changed. Thus, by properly initializing the system, the direction of movement of the catheter will be known at all times.

The present invention further comprises intraluminal devices incorporating preselected markings as just described, as well as sheaths having such preselected markings for placement over unmarked intraluminal probes.

The present invention still further comprises systems for performing the methods as just described. The systems will include an entry structure having an aperture for receiving the medical device therethrough. The entry structure will usually be anchored at or near the desired entry orifice for the device, such as a natural orifice or percutaneous penetration. A means is provided on the entry structure for measuring distance travelled by the device through the aperture in both a forward and a reverse directory, e.g., detecting (usually optically detecting) individual marks on the device as they pass through the aperture. Alternatively, the measuring means will include a roller rotatably mounted within the entry structure adjacent to the aperture which contacts the device as said device passes through the aperture. The roller will usually have annularly spaced-apart markings or structural elements visible on at least one side thereof, and means for detecting passage of these will also be provided on the entry structure. The detecting means for both alternatives will produce a signal in response to passage of the markings, where the signal may have readily distinguishable characteristics depending on the preselected characteristic of the marking. The system will further include circuit means responsive to the signals for generating a digital output which, in turn, can be sent to a dedicated digital display or to other monitoring equipment having the means to provide the digital display, usually in combination with other monitoring information.

The entry structure will be secured at or near the entry orifice for the medical device. In the case of vascular catheters, the entry structure can easily be incorporated within an introducer sheath which is provided in the percutaneous penetration to the blood vessel. In the case of orally insertable devices, such as transesophageal probes, the entry structure can be incorporated in an otherwise conventional bite block which is held in the patient's mouth as the device is inserted.

DESCRIPTION OF THE SPECIFIC EMBODIMENTS

The present invention is widely applicable to a variety of medical procedures of the type which employ an intraluminal probe for imaging, diagnostic, or therapeutic procedures. The commonality among such procedures will be the introduction of an elongate device, such as a catheter, endoscope, transesophageal probe, cystoscope, urethroscope, or other conventional probe, through an orifice into an internal body lumen, cavity, or hollow organ. The orifice may be natural, such as the patient's mouth, colon, urethra, or may be performed by percutaneous penetration using conventional techniques, such as the Seldinger technique.

Procedures which may be advantageously performed in conjunction with the method of the present invention include those in the field of cardiology, such as transesophageal ultrasound, intravascular ultrasound, angioscopy, angioplasty, atherectomy, and electrophysiology; those in the field of radiology, such as the mapping of blood vessels feeding tumors, the location of sites for subsequent surgery or interventional radiology, and vascular sampling for hormonal studies, e.g., renal vein renins; those in the field of urology, such as cystoscopy, ureteroscopy, and prostatic ultrasound; those in the field of obstetrics and gynecology, such as hysterosalpingography and endoscopy; those in the field of oncology, such as catheter drug delivery; those in the field of gastroenterology, such as upper and lower gastrointestinal endoscopy; and those in the field of pulmonology, such as bronchoscopy. While this list is representative of a wide variety of procedures which can be performed, it is not intended to be exhaustive and other candidate procedures which may employ the position monitoring method of the present invention will be apparent to those skilled in the art.

Of particular interest to the present invention are procedures which produce a real time visual image, such as ultrasonic imaging procedures, and in particular transesophageal ultrasound (as described in U.S. Pat. Nos. 4,466,443 and 4,633,882, the disclosure of which are incorporated herein by reference) and intravascular ultrasound (as described in U.S. Pat. Nos. 4,794,931 and 5,000,185, the disclosure of which are incorporated herein by reference). By "real time" it is meant that the images produced at the actual time that a body structure is being scanned by the intraluminal probe. In such procedures, it is possible to incorporate the probe penetration and depth information on the imaging screen so that the treating physician will have such information immediately available and readily apparent. Additionally, the penetration depth information can be recorded as part of the primary image information which is displayed on the imaging screen. Thus, a permanent record will be maintained of the probe penetration depth in association with the image over time. Such information is particularly useful in facilitating relocation of a region of interest for subsequent therapeutic or imaging procedures.

The elongate devices employed by the present invention will usually be conventional intraluminal probes, such as vascular catheters, endoscopes, transesophageal probes, and the like, and will generally comprise an elongate tubular body, usually a flexible tubular body, having a proximal end and a distal end. The length of the tubular body will depend on the particular type of device, with lengths in the range from 40 cm to 200 cm being typical. Usually, the distal end of the tubular body will be adapted to perform an imaging or therapeutic function, although in some cases the probe will be a simple tube having one or more lumens to permit aspiration or perfusion, e.g., for drug delivery. The construction of an intraluminal probe for a particular purpose is well described in the medical and patent literature and is well within the ability of the skilled artisan.

According to a first aspect of the present invention, the elongate tubular body of the intraluminal probe may have a plurality of axially spaced-apart markings along at least a portion of its total length. Usually, such markings will extend over at least a major portion of the total length, typically extending over at least 25% of the length, frequently over at least 50% of the length, and often over 75% of the length, or more. The portion of the length which is covered by the markings will depend on the expected insertional range of the device. That is, if it is known that the device will be inserted from 10 cm to 20 cm from the insertional orifice, then the markings on the device need only cover the length of the tubular body which will move past the fixed detection location as the device is incrementally advanced and withdrawn in the body lumen as described in more detail hereinbelow.

The markings will be formed on the tubular body in a preselected pattern which will permit the system of the present invention to calculate the penetration distance of the device by observing the individual markings as they pass a fixed location relative to the body lumen. While an almost infinite variety of specific patterns could fulfill this requirement (since the system electronics and/or software could be made to recognize and interpret even irregular patterns of markings), the markings will usually be provided in a regular, repeatable pattern, with the repeatable segments being equally spaced-apart. In this way, as the system hardware and software recognize the passage of each repeatable pattern, the total penetration distance can be incremented or decremented with a known separation distance.

The elongate devices will usually have markings which are provided specifically for optical detection using the system of the present invention. The system, however, can be adapted to utilize other intraluminal probes and catheters which have reference markers intended for visual reading or for any other purpose. In the latter case, it will be necessary to calibrate the system to correctly detect and calculate the elapsed distances.

In other cases, it will be desirable to provide sleeves or sheaths which can be fitted over a conventional probe or catheter and which have the desired pattern of markings, as described below. The use of latex condoms for covering medical probes has become common, and such latex condoms can easily be marked to provide the necessary reference marks for the present invention.

In addition to optically detectable markings, it will be possible to provide markings which are sensed by other means, particularly electronically. For example, the catheter could be provided with embedded wires or be metallized in a particular pattern which would permit electronic field detection of the markings as they pass by a suitable sensor located at a fixed position relative to the body lumen being penetrated. It would also be possible to provide mechanical systems including an element which is reeled in and out simultaneously with the deployment of the intraluminal probe. Such a device would be similar to an electronic tape measure with the reel of the tape measure being located at a fixed position relative to the lumen.

Movement of the intraluminal probe can also be sensed mechanically by use of a roller or other element which contacts the probe as it is inserted and withdrawn within the body lumen. Such mechanical systems would usually comprise at least one roller which is maintained in contact with the probe, frequently being spring-biased against the probe. Optionally, roller assemblies comprising two or more rollers could be used for providing redundancy and cross-checking. Rotation induced in the roller(s) by passage of the probe could then be sensed and related to axial movement of the probe. For example, the roller could be optically encoded to permit optical reading of rotation. Alternatively, rotation could be sensed using a potentiometer, a coil system, or by a variety of other electronic techniques. Of these, optical sensing is preferred since it is highly accurate and does not mechanically interfere with tracking of the probe by the roller.

When markings are employed, the spacing between adjacent markings (either on the device or sheath) will generally determine the accuracy and resolution of the measurement which can be made. A particular advantage of the present invention is that electronic detection can resolve even very closely spaced markings. Usually, the markings will be spaced-apart by 1 cm or less, more usually being spaced-apart by less than 5 mm, and in some cases by 2 mm or less. In general, the level of desired resolution will determine the necessary spacing between markings.

The geometry of the markings is not critical, and the individual geometry for single markings may vary on a particular elongate device. Preferably, however, the markings will be annular rings which circumscribe the probe through a transverse plane, i.e., a plane which cuts through the probe normal to the axial direction. Such a ring geometry is advantageous since it is equally visible from all points around the catheter and equally distant from the distal and proximal ends of the catheter.

In most cases, the markings will be optically detectable by conventional optical sensors, as described in more detail hereinbelow. Thus, the markings can be formed by making changes in color, reflectivity, refractivity, and the like, on the outer surface of the tubular body of the elongate device. Conveniently, the markings can be formed by painting, etching, engraving, or otherwise modifying the surface to form the desired geometry. Alternatively, the markings can be formed by the use or radiopaque rings of the type conventionally employed in fabricating vascular catheters and other devices which are observed by fluoroscopic imaging. In such cases, the spaced-apart markings will enhance visibility of the catheter when viewed fluoroscopically in addition to providing the indicia necessary for monitoring penetration depth according to the present invention.

While the detection of the markings will usually be performed optically, it will also be possible to employ magnetic, radioactive, or other similar markings which can be detected using suitable non-optical detectors.

Penetration distance may be measured from any datum point in or relative to the body lumen. Frequently, but not necessarily, the datum point will be the fixed location from which the passage of markers is optically detected. In many cases, however, it may be preferable to measure penetration from an anatomical landmark, such as the coronary ostium (for vascular catheters), the ureteral orifice (for ureteral catheters), the carina tracheae (for bronchial probes), and the like. To measure from such datums, it is necessary that the arrival of the elongate device at the datum be detectable, either by an associated imaging procedure (e.g., fluoroscopic or ultrasonic) or otherwise. Once the elongate device is known to be at the datum, the monitoring and display circuitry can be "zeroed" so that all future distance values will be relative to the datum. The use of anatomical landmarks as datums is advantageous since variations in the entry point of the device will not affect the penetration distance.

Figure 1:
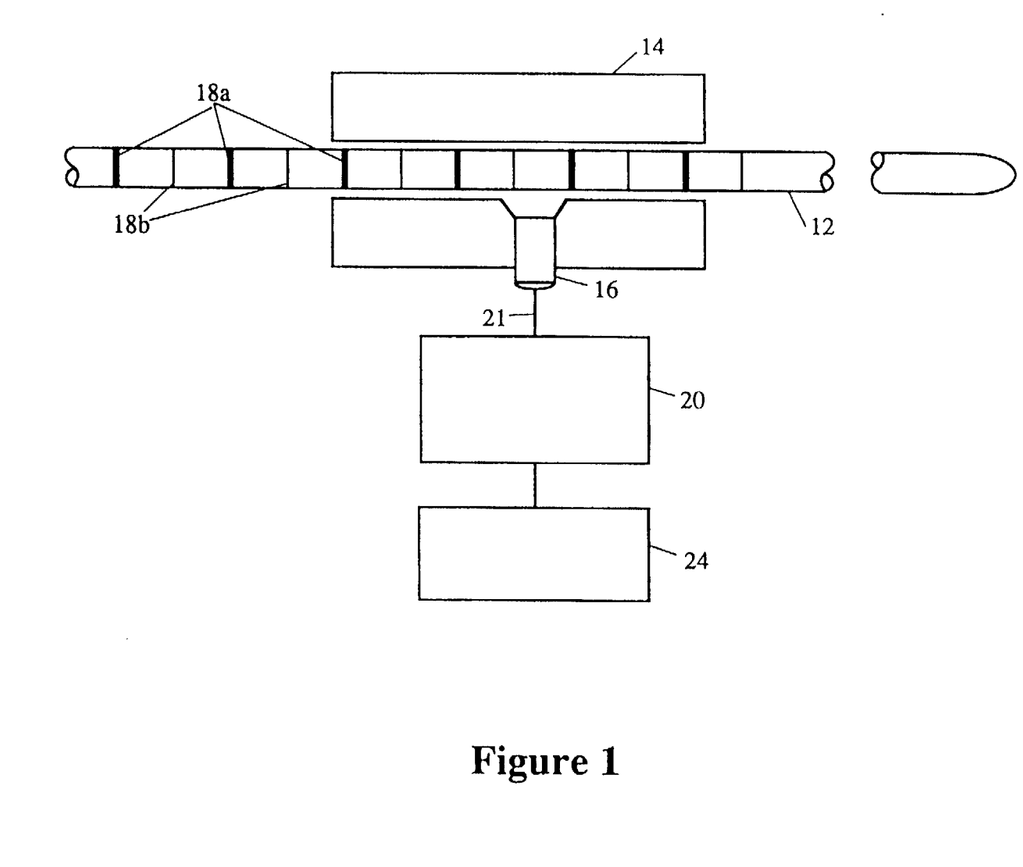
FIG. 1 is a schematic block diagram illustrating the components of a system constructed in accordance with the principles of the present invention and comprising an entry structure, means for producing signals in response to the passage of markings through the entry structure, and circuit means for generating a digital output and/or character generation.

Referring now to FIG. 1, a system 10 for monitoring penetration distance of an elongate device 12 into a body lumen (not illustrated) comprises an entry structure 14 having a detector 16 for detecting a plurality of axially spaced-apart markings 18 formed on the exterior surface of the device 12. As illustrated, the markings 18 are colored, i.e., there is a color contrast between the markings and the remaining surface of the device 12, and the detector 16 is an optical detector which produces a signal corresponding to the passage of each of the markings 18 past its location in the entry structure 14. Suitable photodetectors include photodiodes, photoconductive cells, photoresistors, photoswitches, phototransistors, and phototubes. Such photodetectors will combine both a light source and a reflected light detector which together produce an electronic output signal 21 as the marking passes the fixed location.

Figure 3A:
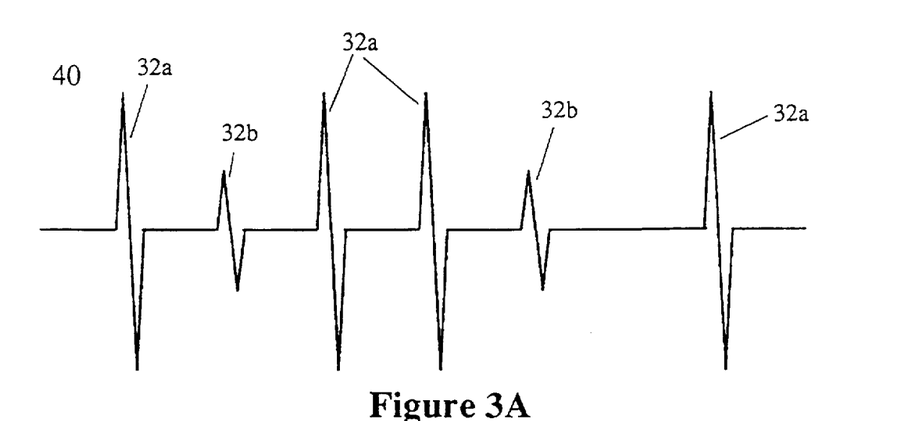
FIG. 3A illustrates a second exemplary signal pattern produced by the signal producing means of the system of FIG. 1.
Figure 3B:
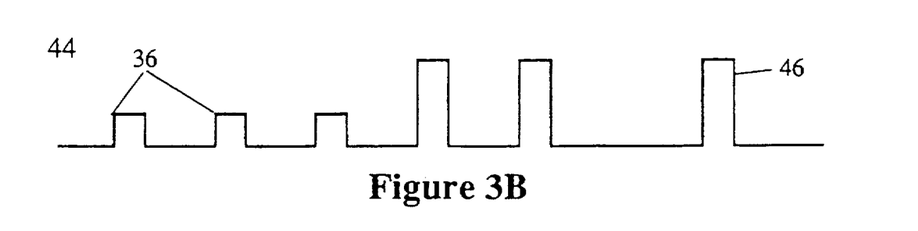
FIG. 3B illustrates an exemplary digital signal pattern produced by the circuit means of the system of FIG. 1 in response to the signal pattern of FIG. 3A.

The signal output of the photodetector 16 is received by signal conditioning circuitry 20 which converts the raw (analog) output from the detector 16 into a suitable digitally encoded form, e.g., NTSC (National Television Systems Committee); NBCD (binary coded decimal), ASCII (American Standard Code for Information Exchange), or the like. The particular code will depend on the type of display or monitor which will be utilized. Conveniently, the circuitry 20 can comprise a conventional analog-to-digital converter which is calibrated to receive a voltage output 21 from the photodetector 16 and convert the voltage level to a digital output 22. As illustrated in FIG. 3 (described hereinafter) the digital output 22 from circuitry 20 will be 0, 1, or 2, representing the most recent passage of a marking.

The digital output 22 of converter 20 is sent to a display or monitor 24 which presents the penetration depth, usually in a digital form. Usually, the display or monitor 24 will include circuitry or software to totalize the digital signal from circuitry 20. In some cases, however, the circuitry 20 will produce an NTSC character signal that may be displayed on a conventional monitor. Frequently, the display or monitor 24 will be part of a separate imaging system, such as an ultrasonic imaging display which presents an ultrasonic image on its display screen simultaneously with the penetration depth.

The markings 18 on elongate device 12 are equally spaced-apart, with broad markings 18a alternating with narrow markings 18b. The markings 18a and 18b are in the form of alternating broad and narrow rings in order to produce a distinct analog output 21 from detector 16, depending on the nature of the marking. By distinguishing between the nature of successive markings which pass by the detector 16, the system 10 can determine in which direction the elongate device 12 is moving so that the net penetration distance can be calculated at all times.

Figure 2A:
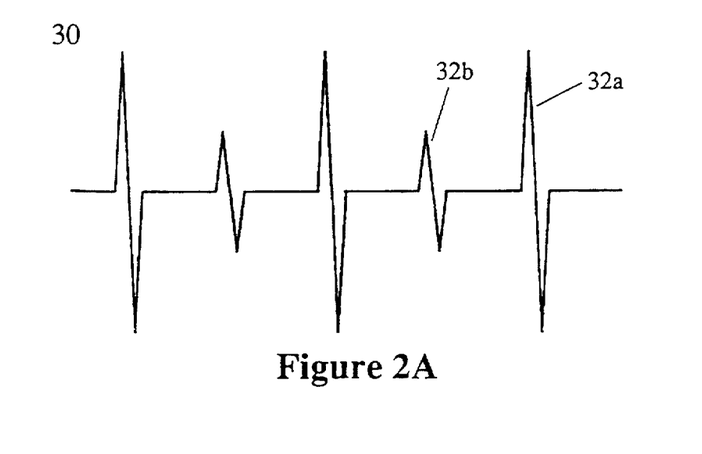
FIG. 2A illustrates an exemplary output from the signal producing means of FIG. 1.

Referring now to FIG. 2A, an exemplary analog output 21 from photodetector 16 is illustrated. The output 30 consists of both large voltage peaks 32a and smaller voltage peaks 32b. The pattern illustrated in FIG. 2A corresponds to the device 12 being inserted through entry structure 14 in a single direction at a generally uniform rate. Thus, the large voltage peaks 32a and lower voltage peaks 32b will alternate and be spaced generally equally apart.

Figure 2B:
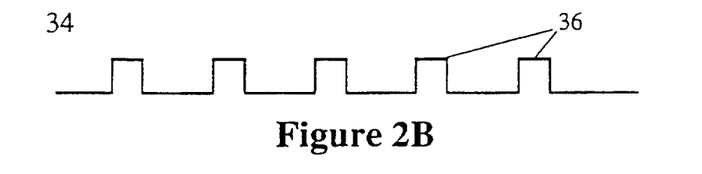
FIG. 2B illustrates an exemplary digital output produced by the circuit means of the system of FIG. 1 in response to the signals of FIG. 2A.

The circuitry 20 will be selected to produce a series of digital signals (0, 1, 2) in response to such a pattern, as illustrated in FIG. 2B. The digital signals can be totalized, either by dedicated accumulator circuitry which is part of detector circuitry 20 or by hardware or software which forms part of the monitor or display means 24. It will be appreciated that each signal 36 in pattern 34 represents movement of the device 12 by a distance equal to that between adjacent markings 18. Each signal 36 is a digital 1 separated by a digital 0, indicating that the markings 18a and 18b are passing the detector in a first direction.

Referring now to FIG. 3A, a pulse pattern 40 which is characteristic of a reversal in direction of the movement of device 12 is illustrated. As the device 12 moves in the first direction, high voltage peaks 32a and low voltage peaks 32b will alternate, in a pattern similar to that seen in FIG. 2A. As the direction of movement reverses, however, a pair of identical peaks 32a or 32b will appear, depending on whether a broad stripe 18a or narrow stripe 18b passes before the detector 16 in both directions. The pattern of large voltage peaks 32a and lower voltage peaks 32b will then continue in an alternating pattern as before. The detection circuitry 20, however, will recognize the reversal in direction and will modify the digital output pattern 44, as illustrated in FIG. 3B. There, incremental movement in the first direction is illustrated by a digital 1 output 36 while an incremental movement in the opposite direction is indicated by a digital 2 output 46. The signals 36 and 46 will again be separated by digital 0. In this way, the monitoring circuitry and/or software incorporated either as part of circuitry 20 or in monitor 24, can sample the digital output at appropriate time intervals and accumulate the net distance traveled by the device 12 for display.

It will be appreciated that the circuitry and software employed by the system 10 can vary widely, depending on the desired type of display and the processing capability of associated systems, such as ultrasonic display equipment.

Figure 4:
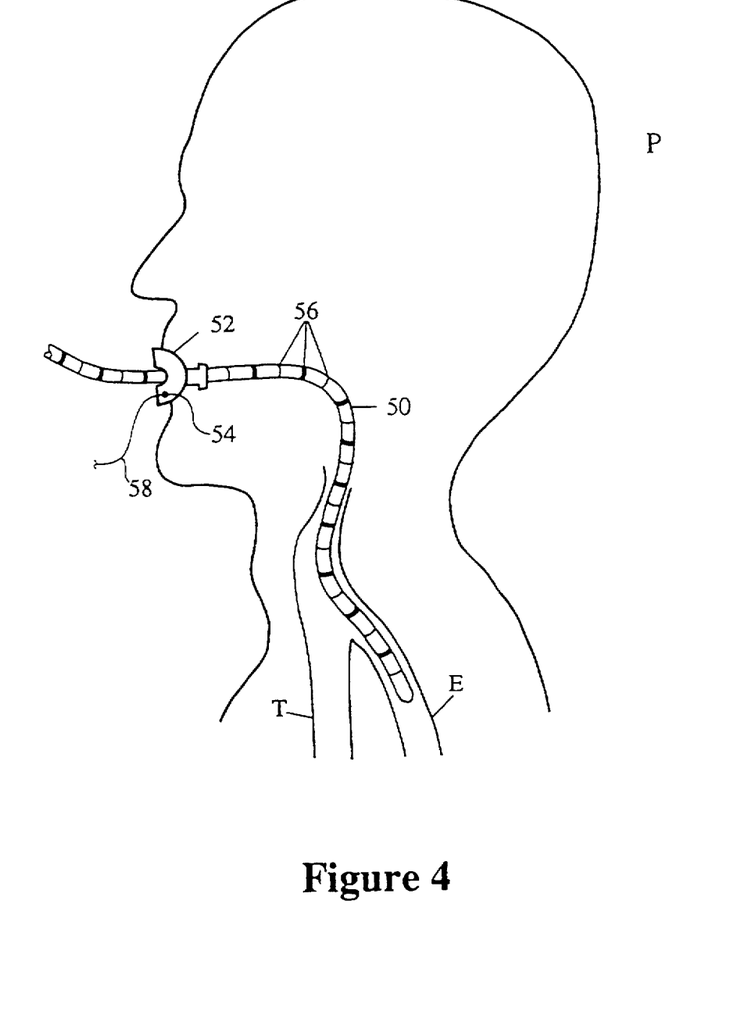
FIG. 4 illustrates a transesophageal probe being introduced through a bite block according to the method of the present invention.

Referring now to FIG. 4, a transesophageal probe 50 which is introduced into the esophagus E of patient P is illustrated. The transesophageal probe 50 is introduced through a bite block 52 which incorporates a photosensor 54 to detect markings 56 formed on the probe 50 as just described. A connector wire 58 extends from the photosensor 54 to the associated signal processing circuitry (not illustrated) which is generally described as above in connection with FIG. 1.

Figure 4A:
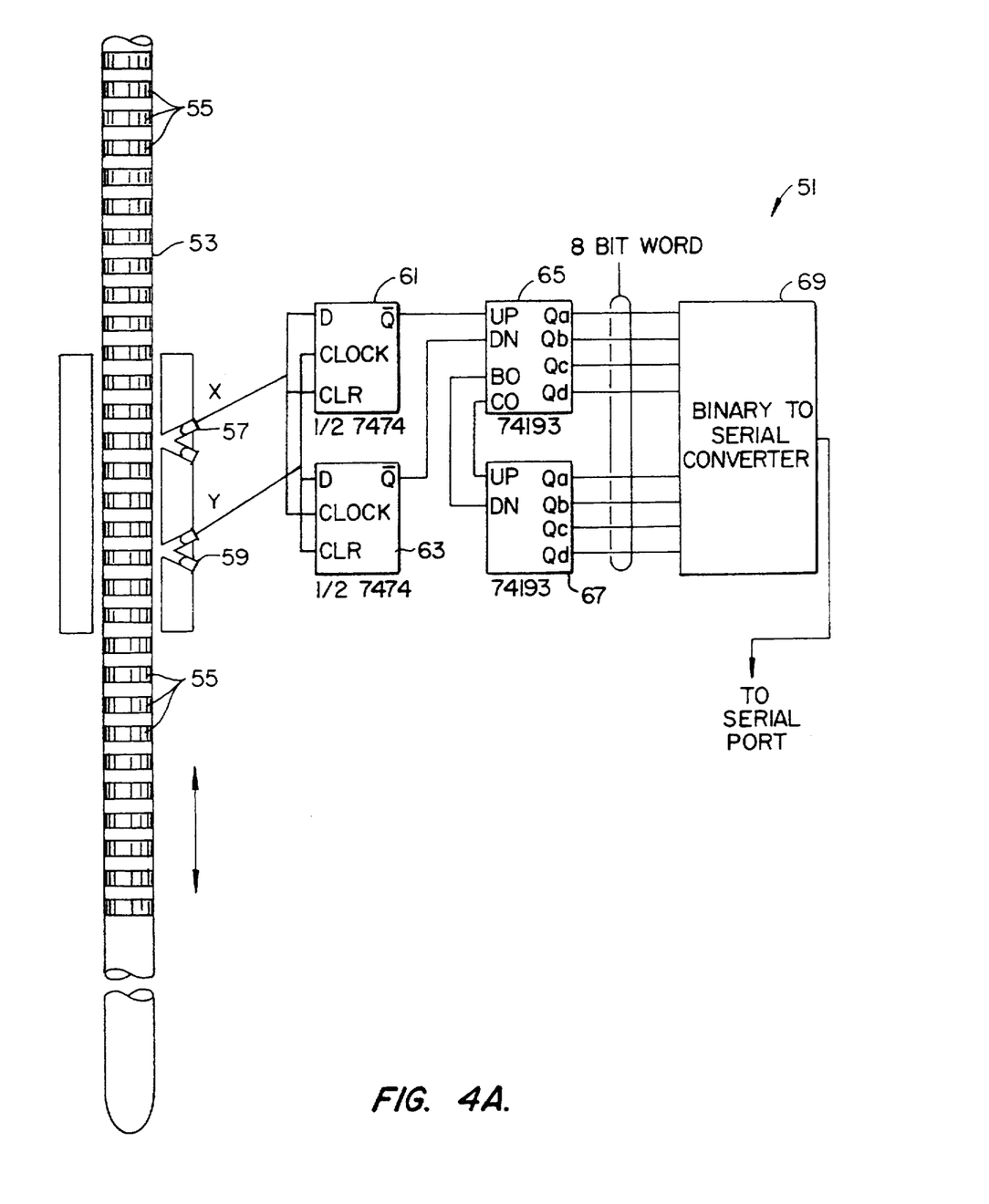
FIG. 4A is a schematic illustration of a probe employing a quadrature detection system constructed in accordance with the principles of the present invention.
Figure 4B:
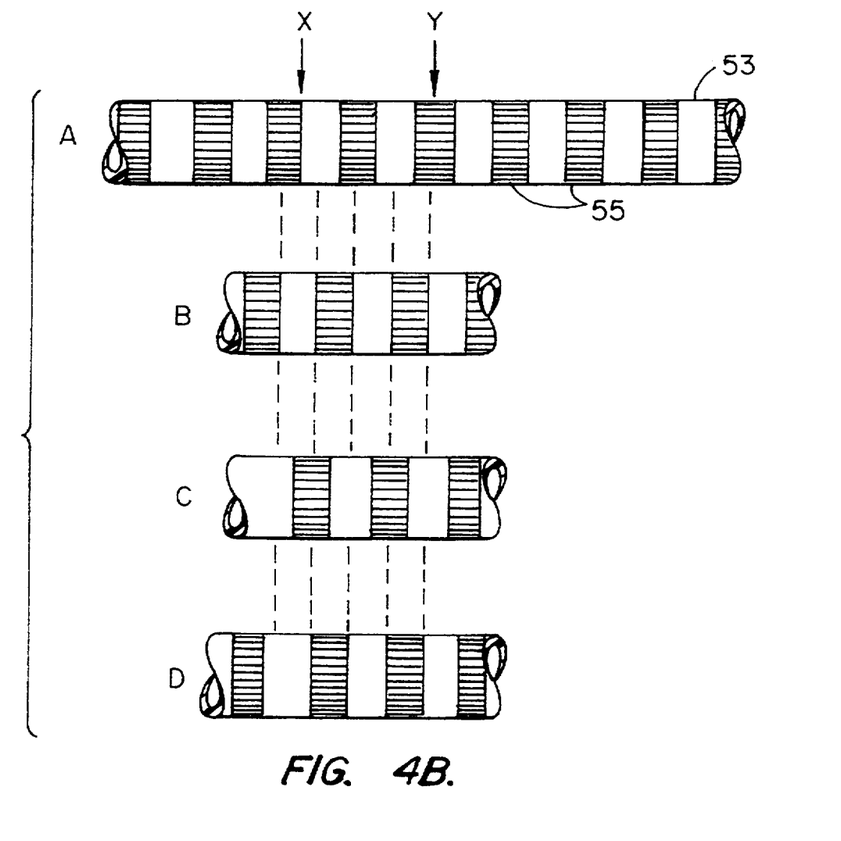
FIG. 4B illustrates the principles of quadrature detection.
Figure 4C:
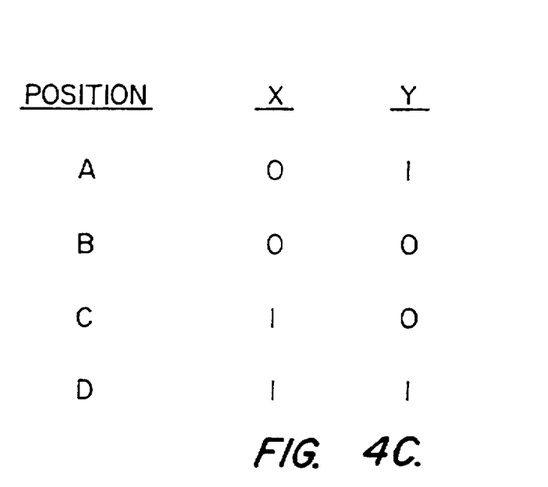
FIG. 4C is a truth table illustrating the digital output of the quadrature detection system of FIGS. 4A and 4B.

Referring now to FIGS. 4A–4C, a preferred system 51 for optically sensing axial movement of an intraluminal probe 53 will be described. A system 51 is designed to provide quadrature detection of passage of the probe. Axially spaced-apart markings 55 on the probe 53 will be arranged in a manner consistent with such quadrature detection, preferably being bands having a constant width which are separated by spaces having the same width as the bands. Detectors 57 and 59 are arranged so that they are out of phase with the spacing of markings 53, preferably being ±90° or ±270° out of phase. As illustrated, the detector 57 is 270° out of phase with detector 59.

Using such a system, it will be appreciated that the detectors will provide a series of four unique output pairs (X,Y) as the probe advances over a distance equal to the width of one marking and one adjacent blank region. As best illustrated in FIGS. 4B and 4C, detectors 57 and 59 will have outputs X and Y, respectively, as illustrated. In position A, detector 57 is just entering a "blank" region between adjacent markings 55 and will have an output which is arbitrarily assigned 0. Detector 59, in contrast, will be aligned with the middle of a marking, providing an output of 1. As the probe moves to position B, detector 57 will continue to observe a blank region of the probe 53, while detector 59 will have moved to the beginning of a blank region. Thus, outputs X and Y will be 0,0. As the probe 53 advances further through a distance equal to one-half-marking length to position C, a marking band 55 will pass into the field of view of detector 57 while detector 59 continues to see a blank region, resulting in an X,Y pair of 1,0. Finally, as the probe 53 moves forward by an additional one-half-marking length, detector 57 will continue to observe a marking 55, while detector 59 begins to observe a new marker 55. Thus, the X,Y pair will be 1,1. In this way, incremental movements equal to one-half-marking length of the probe 53 can be detected.

FIG. 4A further illustrates a suitable quadrature decoding circuit. A pair of D-type flipflops 61 and 63 receive square waves generated by the detectors 57 and 59, respectively. Due to the relative phase of the two signals from the detectors, a string of pulses emerges from either the upper or lower output Q. These are fed into "up" and "down" inputs of a synchronous up-/down counter (74193). The carry and borrow pins are connected directly to up and down inputs of a second counter (74193). The combined outputs present binary data to a parallel series converter 69, which provides a serial output to a host system controller, such as the controller for an ultrasound system.

Referring to FIG. 4A, detectors 57 and 59 typically comprise an illumination source and a reflected light detector. The outputs X and Y are either "high" or "low" depending on the alignment of the markings 55 and spaces 53, and are attached to inputs D and CLOCK and CLEAR of the D-type flip-flops 61 and 63 as shown. The D-type flip-flops 61 and 63 each have outputs Q. In general, if the CLR input is low, the Q is set to the value present at input D when the CLOCK transitions from low to high. If the CLR input is high, then Q is set to low. Q is always the logical opposite of Q. In general, the output of the up/down counter 65 increments in response to pulses presented to inputs UP or DN. It's carry and borrow pins C0 and B0 are used to cascade the count to the UP and DN inputs of counter 67. The net output of this circuit in response to an insertion of the probe is a string of pulses from the output Q of flipflop 61. In response to an extraction, the circuit produces a string of pulses from output Q of flipflop 67. These two streams of pulses are totalized by the counter 65.

It will be appreciated that the resolution of the detector system 51 can be further refined by providing additional detectors. An arbitrary number (N) of sensor pairs may be located with relative phase angles of ±180°/N. Such an arrangement can provide a spatial resolution of L/2N where L is equal to the combined length of a band and the adjacent blank region. Spatial resolution may be further increased by decreasing the width of the band and associated blank region, although the latter approach is limited by the ability of the sensors to detect very narrow bands.

Instead of using discrete optical sensors, as illustrated in FIGS. 4A–4C, it would be possible to utilize a fiberoptic sensor connected to a charge-coupled diode (CCD) array. The positions of the markings over time could be determined using basic image processing technology, with discrete images being compared with prior images to determine the distance (and optionally rotational angle) which the intraluminal probe has moved over the time interval.

Figure 5:
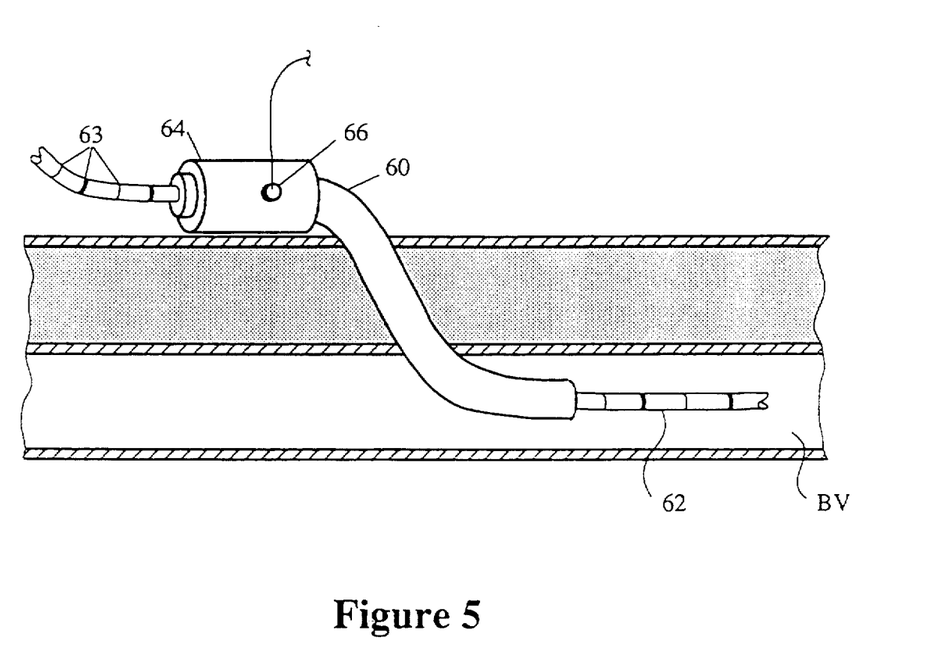
FIG. 5 illustrates an intravascular catheter being introduced through a catheter sheath according to the method of the present invention.

FIG. 5 illustrates a catheter introducer sheath 60 which is used to introduce vascular catheter 62 percutaneously into a blood vessel BY. The catheter sheath 60 includes a housing 64 at its proximal end having a photosensor 66 formed therein. The photosensor 66 is disposed to detect markings 68 on the exterior surface of the catheter 62. The housing 64 will be drawn up to the penetration and the location of photosensor 66 will remain fixed relative to the percutaneous entry orifice and blood vessel BY.

Figure 6:
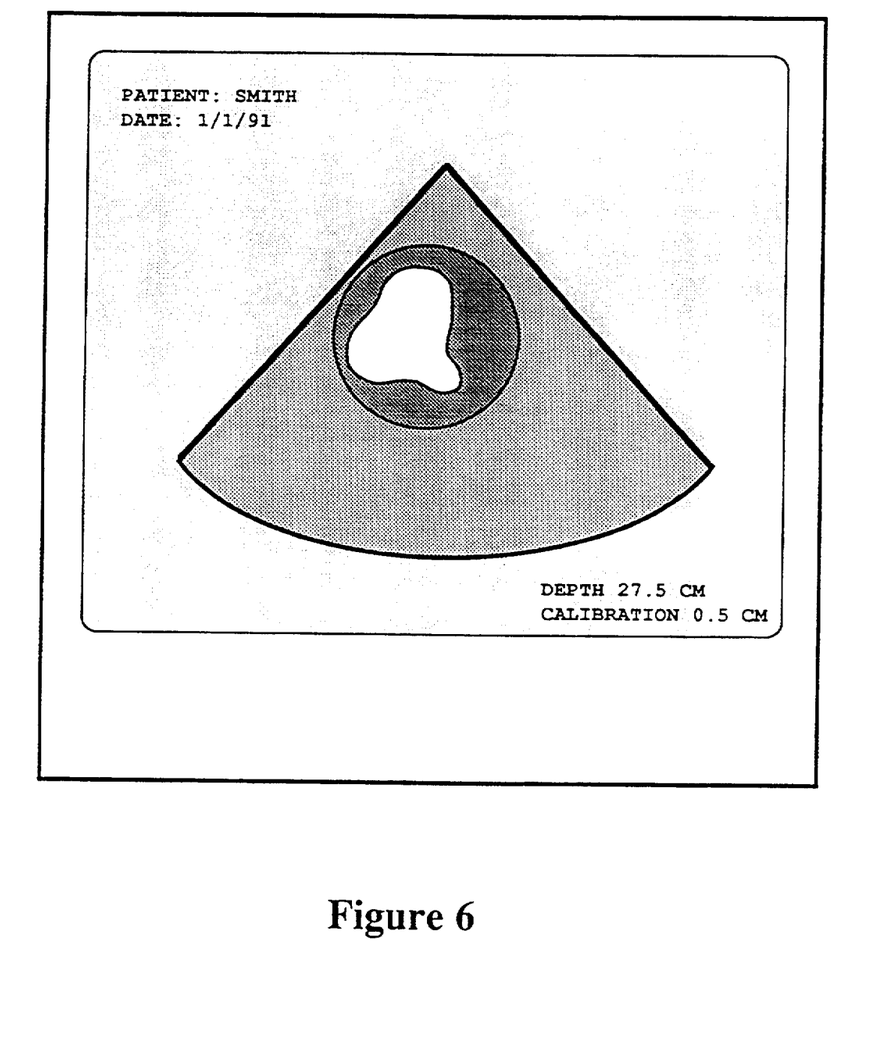
FIG. 6 illustrates an exemplary ultrasonic monitor which incorporates both a cross-sectional image of a blood vessel and the digital penetration information produced by the method and system of the present invention.

Referring now to FIG. 6, an exemplary display monitor 70 which can be used with a vascular ultrasonic imaging catheter, such as that illustrated in U.S. Pat. Nos. 4,794,931 and 5,000,185, is illustrated. The monitor display will contain both a cross-sectional image 72 and penetration depth information 74 simultaneously. Such a display format is particularly advantageous since the treating physician has the visual image information available at the same time as the penetration depth information. Moreover, when the visual information is recorded, such as is commonly performed by video recording, the penetration depth information will be recorded at the same time so that a permanent record is kept which relates the precise penetration depth to the image which appears on the screen at any time.

Figure 7:
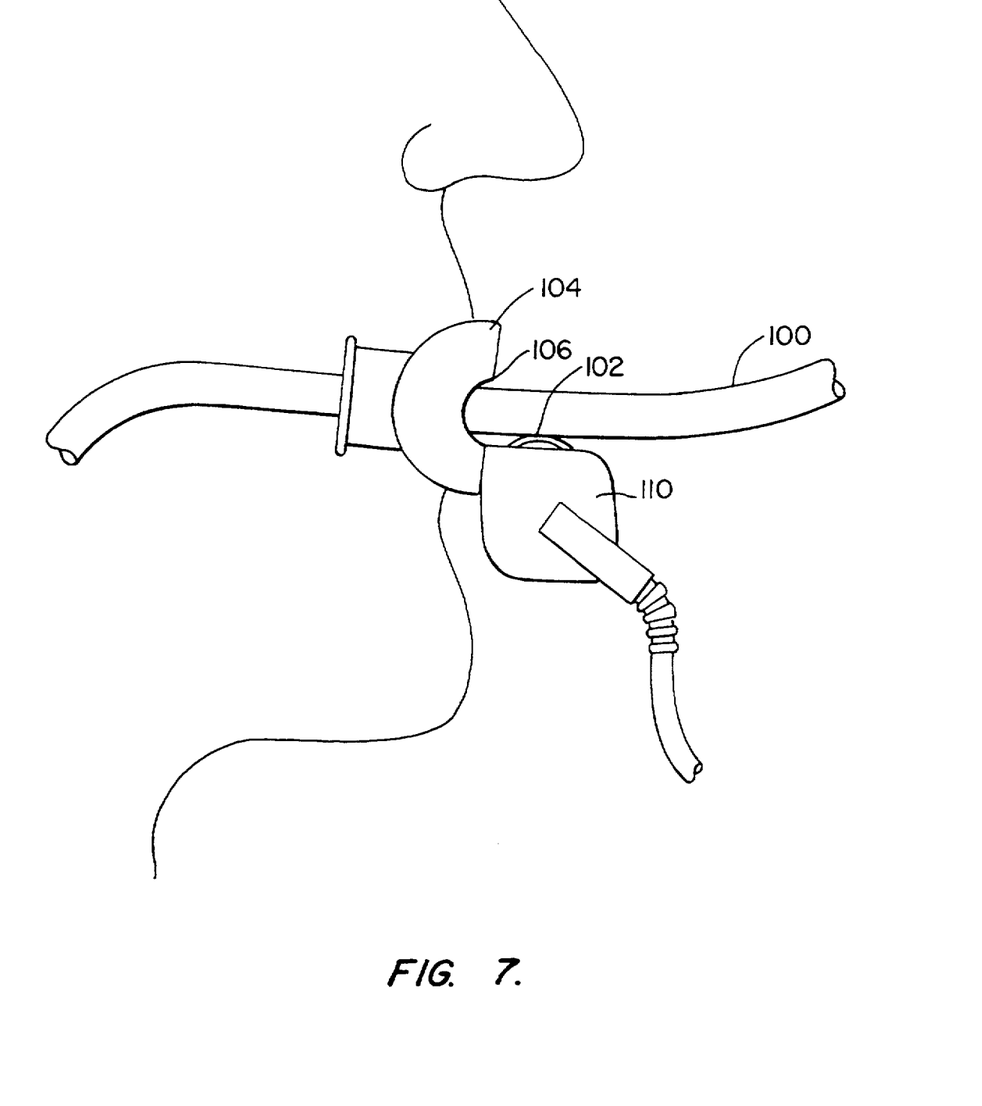
FIG. 7 illustrates an alternative embodiment of a device penetration monitoring system constructed in accordance with the principles of the present invention, where the position of an intraluminal probe is monitored by contact with a roller assembly.
Figure 8:
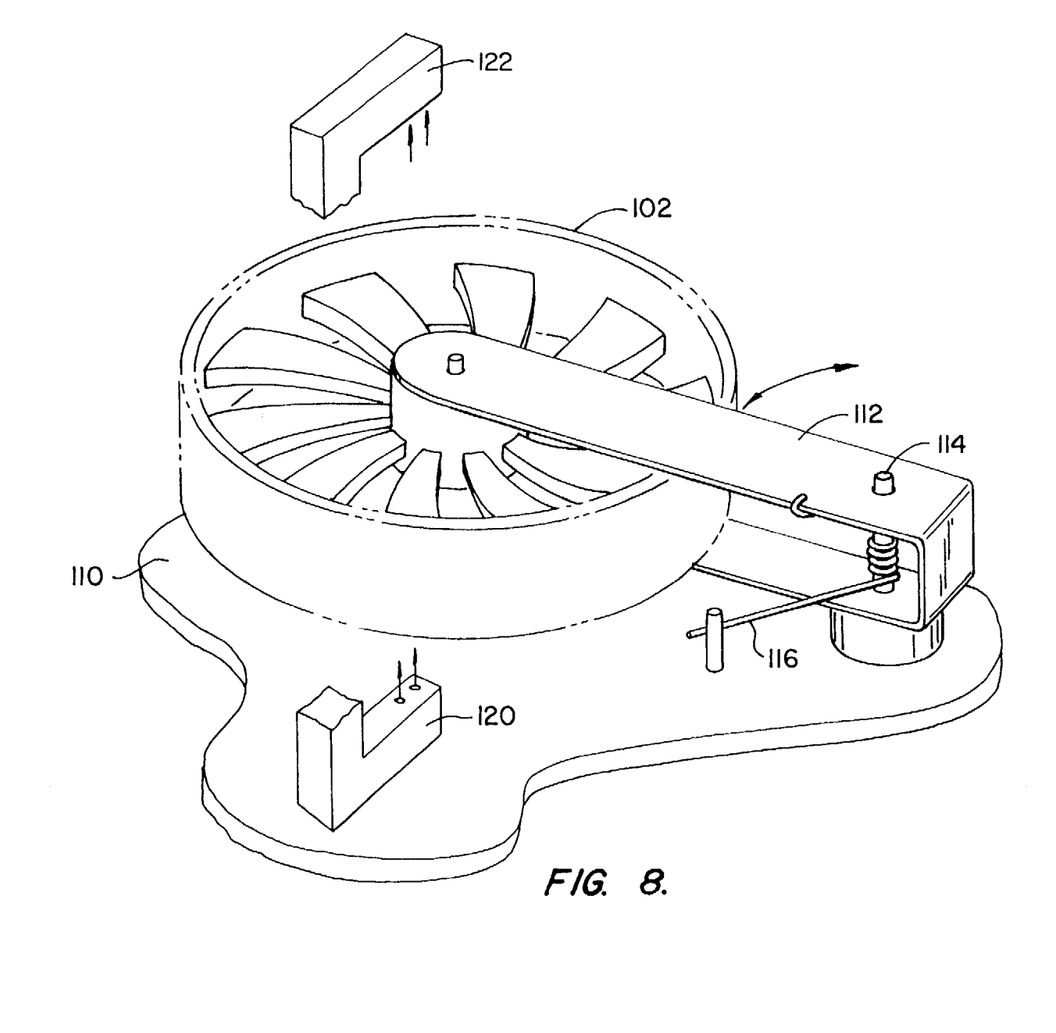
FIG. 8 is a schematic illustration of the roller assembly of FIG. 7, showing an optical system for detecting rotation of the contact roller.

An alternate embodiment of the intraluminal probe penetration monitoring system of the present invention is illustrated in FIGS. 7 and 8. This system relies on contacting a probe 100 with a contract roller 102, as best illustrated in FIG. 7. The roller 102 is mounted adjacent a mouthpiece 104 which act as an entry structure for transesophageal penetration of the probe 100. Mouthpiece 104 includes an aperture 106 which slidably receives the probe 100 therethrough. Roller 102 is mounted in a roller housing 110, as best illustrated in FIG. 8. The roller is mounted on a support arm 112 which is pivotally connected to the housing 110 on a pin 114. A spring 116 is provided to bias the arm 112 so that the roller 102 is urged in an upward direction as illustrated in FIG. 7. The spring bias helps assure that the roller 102 will remain in firm contact against the transesophageal probe 100 as it is advanced and withdrawn from the mouthpiece 104.

It will be appreciated that advancement and withdrawal of the transesophageal probe 100 will cause rotation of the wheel 102 in either the counter-clockwise direction (as the probe is inserted into the esophagus) or the clockwise (as the probe is withdrawn from the esophagus). Detection of such rotation is best performed optically using a pair of light sources 120 and aligned light detectors 122. The roller 102 includes a plurality of generally radial spokes having arcuate leading and trailing edges. The light beams emanating from the light sources 120 are interrupted by rotation of the wheel which causes the spokes to pass through the beams. The arcuate shape of the spokes is selected so that movement of the arm 112 about pivot point 114 will not disturb the length of travel measured by the roller 102. A pair of light sources and associated sensors are employed so that overtravel of the arm 112 can be detected. If the roller 102 travels too far in either direction, one of the sensors will become blocked by the hub or rim of the wheel, and the associated circuitry can detect such overtravel. The circuitry described in connection with FIG. 4A, above, would be suitable.

Although the foregoing invention has been described in detail for purposes of clarity of understanding, it will be obvious that certain modifications may be practiced within the scope of the appended claims.

What is claimed is:

1. A method for monitoring penetration distance of an elongate device into a body lumen as the device is advanced and withdrawn within the lumen, said method comprising:
   detecting axially spaced-apart markings on the device as such markings pass by a location which is fixed relative to the lumen;
   producing an electronic output signal in response to the passage of each marking; and
   totalizing the signals to produce a value which corresponds to the penetration distance in real time.

2. A method as in claim 1, wherein the markings are optically detected.

3. A method as in claim 1, wherein the signals are totalized by determining the direction of movement of the device and incrementing or decrementing the accumulated distance based on the number of signals and direction of movement.

4. A method as in claim 3, wherein the accumulated distance is set to zero when a location on the device reaches an anatomical landmark in the body lumen, whereby all subsequent real time distance values are relative to the landmark.

5. A method as in claim 4, wherein the direction of movement is determined by comparing a preselected characteristic of successive marking which pass by the location and determining direction based on preselected patterns of said characteristics.

6. A method as in claim 5, wherein the markings are rings and the predetermined characteristic is ring width and the preselected pattern is alternate broad and narrow width, wherein the detection of successive rings having alternating widths indicates movement in a constant direction and the detection of successive rings having the same widths indicates a reversal of direction.

7. A method as in claim 1, further comprising displaying the real time value.

8. A method as in claim 7, wherein the real time value is displayed on a screen which simultaneously displays a real time image.

9. A method as in claim 8, further comprising recording the combined real time image and real time value.

10. A method for monitoring penetration distance of an elongate device into a body lumen as the device is advanced and withdrawn within the lumen, said method comprising:
  measuring distance traveled as the elongate device is advanced one or more times past a location which is fixed relative to the lumen;
  measuring distance traveled as the elongate device is withdrawn one or more times past the fixed location;
  producing an electronic output signal for each of the measured distances; and
  continuously totalizing the signals corresponding to the distance advanced and the distance withdrawn to produce a value which corresponds to the net penetration distance in real time.

11. A method as in claim 10, wherein the distance traveled is measured by optical detection of axially spaced-apart markings on the device as such markings pass by the location which is fixed.

12. A method for monitoring penetration distance of an elongate device into a body lumen as the device is advanced and withdrawn within the lumen, said method comprising:
  measuring distance traveled as the elongate device is advanced one or more times past a location which is fixed relative to the lumen;
  measuring distance traveled as the elongate device is withdrawn one or more times past the fixed location;
  continuously totalizing the distance advanced and the distance withdrawn to produce a value which corresponds to the net penetration distance in real time; and
  visually displaying in real time the value corresponding to the net penetration distance.

* * * * *